United States Patent [19]

Moore

[11] Patent Number: 4,785,019
[45] Date of Patent: Nov. 15, 1988

[54] N-CYANOALKYL-N-HALOALKYLTHIO CARBOXAMIDES AS FUNGICIDES

[75] Inventor: Joseph E. Moore, Richmond, Calif.

[73] Assignee: Chevron Research Company, San Francisco, Calif.

[21] Appl. No.: 833,948

[22] Filed: Feb. 27, 1986

Related U.S. Application Data

[63] Continuation-in-part of Ser. No. 736,497, May 21, 1985, abandoned, which is a continuation of Ser. No. 655,483, Sep. 27, 1984, abandoned.

[51] Int. Cl.$^4$ .................. A01N 37/28; C07C 121/417; C07C 121/52
[52] U.S. Cl. .................. 514/521; 514/528; 558/392; 558/430; 558/434; 558/436
[58] Field of Search .............. 558/392, 430, 434, 436; 514/521, 528

[56] References Cited

U.S. PATENT DOCUMENTS 4,151,353 4/1979 Thurman .......................... 558/436
4,652,556 3/1987 Moore et al. .................... 558/434

Primary Examiner—Anton H. Sutto
Attorney, Agent, or Firm—S. R. La Paglia; R. C. Gaffney; S. L. Biggs

[57] ABSTRACT

N-cyanoalkyl-N-haloalkylthio alkyl-, aryl- and aralkyl-carboxamides of the general formula:

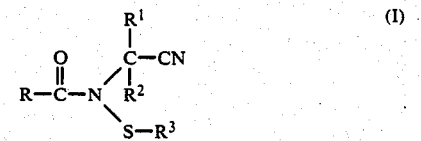

wherein R is alkyl of 1 to 10 carbon atoms, cycloalkyl of 3 to 10 carbon atoms, lower alkenyl of 2 to 6 carbon atoms or lower alkynyl of 2 to 6 carbon atoms, all optionally substituted with 1 to 4 halogen atoms; lower alkoxyalkylene; aryl of 6 to 12 carbon atoms; aralkyl of 7 to 16 carbon atoms; or substituted aryl or substituted aralkyl both substituted with 1 to 3 substituents independently selected from phenyl, lower alkyl of 1 to 6 carbon atoms, lower alkoxy of 1 to 6 carbon atoms, lower alkylthio of 1 to 6 carbon atoms, halogen, nitro, cyano,

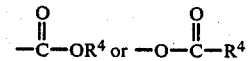

wherein $R^4$ is hydrogen or lower alkyl of 1 to 6 carbon atoms,

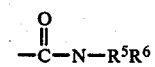

wherein $R^5$ and $R^6$ are independently hydrogen or lower alkyl of 1 to 6 carbon atoms; $R^1$ and $R^2$ are independently hydrogen, or lower alkyl of 1 to 6 carbon atoms; and $R^3$ is alkyl of 1 to 3 carbon atoms substituted with 3 to 6 halogen atoms or trihalovinyl are fungicidal.

26 Claims, No Drawings

N-CYANOALKYL-N-HALOALKYLTHIO CARBOXAMIDES AS FUNGICIDES

CROSS REFERENCE TO RELATED APPLICATIONS

This application is a continuation-in-part of U.S. Ser. No. 736,497, filed May 21, 1985, which is a continuation of application U.S. Ser. No. 655,483, filed Sept. 27, 1984, both now abandoned.

BACKGROUND OF THE INVENTION

The present invention relates to novel N-cyanoalkyl-N-haloalkylthio alkyl-, aryl- and aralkylcarboxamides which are active as fungicides.

Certain N-substituted polyhaloalkylthio phthalimides, cycloalkyl and cycloalkenyldicarboximides, hydantoins and sulfonamides have been disclosed as fungicides. See, e.g., commonly-assigned U.S. Pat. No. 3,178,447 and U.S. Pat. No. 4,511,735.

In addition, certain N-tetrachloroethylthio sulfonamides have been disclosed as having activity as miticides and mite ovicides. See, e.g., commonly-assigned U.S. Pat. No. 4,350,831.

Commonly assigned patent application "Fungicidal N-Cyanoalkyl-N-Haloalkylthio Sulfonamides", U.S. Ser. No. 767,009, discloses certain N-cyanoalkyl N-polyhaloalkyl sulfonamides as fungicidal.

SUMMARY OF THE INVENTION

The fungicidal N-cyanoalkyl-N-haloalkylthio alkyl-, aryl- and aralkyl-carboxamides of the present invention may be represented by the general formula:

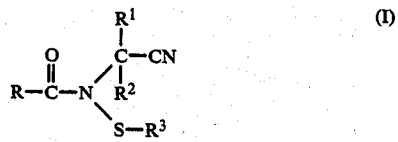

wherein R is alkyl of 1 to 10 carbon atoms, cycloalkyl of 3 to 10 carbon atoms, lower alkenyl of 2 to 6 carbon atoms or lower alkynyl of 2 to 6 carbon atoms, all optionally substituted with 1 to 4 halogen atoms; lower alkoxyalkylene; aryl of 6 to 12 carbon atoms; aralkyl of 7 to 16 carbon atoms; or substituted aryl or substituted aralkyl both substituted with 1 to 3 substituents independently selected from phenyl, lower alkyl of 1 to 6 carbon atoms, lower alkoxy of 1 to 6 carbon atoms, lower alkylthio of 1 to 6 carbon atoms, halogen, nitro, cyano,

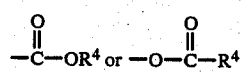

wherein $R^4$ is hydrogen or lower alkyl of 1 to 6 carbon atoms,

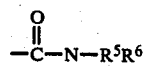

wherein $R^5$ and $R^6$ are independently hydrogen or lower alkyl of 1 to 6 carbon atoms; $R^1$ and $R^2$ are independently hydrogen, or lower alkyl of 1 to 6 carbon atoms; and $R^3$ is alkyl of 1 to 3 carbon atoms substituted with 3 to 6 halogen atoms or trihalovinyl.

Among other factors, the present invention is based on my finding that these compounds are effective as fungicides against a variety of fungi. In particular, these compounds are effective in controlling certain fungal diseases in plants.

Preferred R groups include naphthyl, phenyl or phenyl substituted with 1 or 2 substituents. Preferred substituted phenyl groups include ortho-substituted phenyl groups and includes, for example, 0-tolyl, 0-carbomethoxy.

Preferred $R^1$ and $R^2$ groups include hydrogen and methyl.

Preferred $R^3$ groups include those where the halogen substituents are chlorine or chlorine and fluorine, and include, for example, trichloromethyl, 1,1,2,2-tetrachloroethyl, 1,2,2,2-tetrachloroethyl, trichlorovinyl, 2-fluoro-1,1,2,2-tetrachloroethyl, and fluorodichloromethyl. Especially preferred $R^3$ groups include 1,1,2,2-tetrachloroethyl.

The especially preferred halogen is chlorine.

Definitions

As used herein, the following terms have the following meanings unless expressly stated to the contrary.

The term "alkyl" refers to both straight- and branched-chain alkyl groups. The term "lower alkyl" refers to both straight- and branched-chain alkyl groups having a total of from 1 to 6 carbon atoms and includes primary, secondary and tertiary alkyl groups. Typical lower alkyls include, for example, methyl, ethyl, n-propyl, isopropyl, n-butyl, isobutyl, t-butyl, n-pentyl, n-hexyl, and the like.

The term "cycloalkyl" refers to cyclic alkyl groups. The term "lower cycloalkyl" refers to groups having from 3 to 6 carbon atoms in the ring, and includes cyclopropyl, cyclobutyl, cyclopentyl, and cyclohexyl.

The term "alkylene" refers to the group —$(CH_2)_m$— wherein m is an integer greater than zero. Typical alkylene groups include, methylene, ethylene, propylene, and the like.

The term "alkylthio" refers to the group R'S— wherein R' is alkyl. The term "lower alkylthio" refers to alkylthio groups having 1 to 6 carbon atoms; examples include methylthio, ethylthio, n-hexylthio, and the like.

The term "alkoxy" refers to the group —OR' wherein R' is an alkyl group. The term "lower alkoxy" refers to alkoxy groups having from 1 to 6 carbon atoms; examples include methoxy, ethoxy, n-hexoxy, n-propoxy, isopropoxy, isobutoxy, and the like.

The term "alkoxyalkylene" refers to groups having the formula R'OR"— wherein R' is alkyl and R" is straight- or branched-chain alkylene. The term "lower alkoxyalkylene" refers to alkoxyalkylene groups where R' is lower alkyl and R" has a chain length of up to 6 carbon atoms. Typical lower alkoxyalkylene groups include, for instance, methoxymethylene, methoxypropylene, isopropoxybutylene, hexoxyethylene, and the like.

The term "alkenyl" refers to unsaturated alkyl groups having a double bond [e.g., $CH_3CH=CH(CH_2)_2$—] and includes both straight- and branched-chain alkenyl groups. "Lower alkenyl" refers to groups having a total of from 2 to 6 carbon atoms. Typical lower alkenyl groups include, for example, vinyl, propenyl, but-3-enyl, hex-4-enyl, 2-methyl-pent-4-enyl, and the like.

The term "halo" or "halogen" refers to the groups fluoro, chloro, bromo, and iodo.

The term "haloalkenyl" refers to alkenyl groups substituted with from 1 to 3 halogen atoms. "Lower haloalkenyl" refers to groups having a total of from 2 to 5 carbon atoms, and includes, for example, 1-chloropropenyl, 2,3-dibromo-but-3-enyl, and the like.

The term "alkynyl" refers to unsaturated alkyl groups having a triple bond (e.g., $CH_3C\equiv CCH_2-$) and includes both straight- and branched-chain alkynyl groups. "Lower alkynyl" refers to groups having a total of from 2 to 5 carbon atoms. Typical lower alkynyl groups include propynyl, butynyl, and the like.

The term "hydroxy alkyl" refers to the group $-R'-OH$ wherein $R''$ is branched or unbranched alkylene and the hydroxy can be on a primary, secondary or a tertiary carbon. Examples include hydroxyethyl and 2-hydroxypropyl and 2-hydroxy-2-methyl butyl.

The term "aryl" refers to aryl groups having from 6 to 12 carbon atoms and includes, for example, phenyl, p-chlorophenyl, m-methylphenyl, p-butylphenyl, m-trifluoromethylphenyl, naphthyl, and the like.

The term "aralkyl" refers to an alkyl group of 1 to 4 carbons substituted with an aryl group of from 6 to 12 carbons and includes, for example, benzyl, p-chlorobenzyl, p-methylbenzyl, and 2-phenylethyl.

The term "alkylamino" refers to the group $R'R''N-$ wherein $R'$ is alkyl and $R''$ is hydrogen or alkyl. The term "lower alkylamino" refers to alkylamino groups having 1 to 6 carbon atoms. Typical alkylamino groups include methylamino, ethylamino, diethylamino, dimethylamino, and the like.

Pests are any insect, rodent, nematode, fungus, weed, or any form of terrestrial or aquatic plant or animal life or virus, bacterial organism or other microorganism (except those viruses, bacteria or other microorganisms existing in living humans or other living animals) considered injurious to health, the environment or man's economic well-being.

DETAILED DESCRIPTION OF THE INVENTION

The compounds of the present invention may be conveniently prepared according to the following reaction scheme:

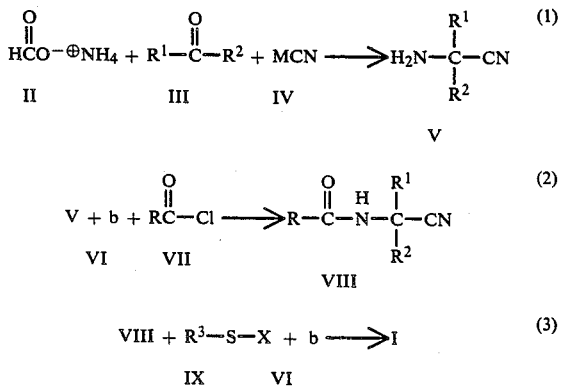

wherein R, $R^1$, $R^2$ and $R^3$ are as previously defined in conjunction with Formula I, M is an alkali metal ion, b is a base, and X is halogen.

Reaction (1) involves addition of an amino and a cyano group to carbonyl-containing intermediate III. Various conventional ammonia sources (amination reagents) may be used. Suitable reagents include ammonium formate, ammonium acetate, ammonium carbonate, and ammonium chloride/ammonium hydroxide. Other conventional sources of ammonia may be used.

By way of illustration, ammonium formate is used as the ammonia source. Thus, reaction (1) is conducted by combining approximately equimolar amounts of II, III and IV in solvent. Although the reactants may be added in any order, it is preferred to add IV to a stirred solution of II and III in solvent. Reactant (II) may be prepared in situ from formic acid. Suitable solvents include water. The reaction is conducted at a temperature of about 0° C. to about 50° C., preferably from about 5° C. to about 30° C., and is generally complete within about 1 to about 4 hours. The product V is isolated by conventional procedures such as extraction, distillation, column chromatography and the like. Alternatively, V may be isolated as a salt, such as the hydrochloride, by precipitation.

Reaction (2) is conducted by combining approximately equimolar amounts of V, VI and VII in solvent. Although the reactants may be combined in another order, it is preferred to add VII to a stirred mixture of V and VI in solvent. Certain examples of V, or its salts are commercially available and may be used rather than preparing V according to Reaction (1). Although approximately equimolar amounts of V, VI and VII may be used, it is preferred to use a slight excess of VI in relation to V and VII, on the order of about 1.1 to about 1.2 equivalents VI per equivalent of V/VII. Suitable bases include organic bases such as triethylamine, pyridine, and the like or inorganic bases, such as sodium hydroxide, potassium hydroxide or the like. Suitable solvents include inert organic solvents such as methylene chloride, chloroform, benzene, or the like, and water. The reaction is conducted at a temperature of about 0° C. to about 50° C., preferably from about 5° C. to about 30° C. and is generally complete within about 0.25 to about 1 hour. The product, VIII, is isolated by conventional procedures such as washing, stripping, filtration, crystallization, chromatography, and the like.

Reaction (3) is conducted by combining VIII, IX and VI in solvent. Although the reactants may be combined in different order, it is preferred to add VI in solvent to a stirred mixture of VIII and IX in solvent. Although approximately equimolar amounts of VI, VIII and IX may be used, it is preferred to use a slight excess of VI in relation to VIII and IX, on the order of about 1.1 to about 1.2 mole VI per mole VIII and IX. Suitable bases VI include organic bases such as triethylamine, pyridine and the like or inorganic bases, such as sodium hydroxide, potassium hydroxide, and the like. Suitable solvents include water, or organic solvents such as methylene chloride, chloroform, and the like. The reaction is conducted at a temperature of about 0° C. to about 50° C., preferably from about 5° C. to about 35° C., or for convenience at ambient temperature. The reaction is generally complete in about 0.25 to about 1 hour. The product, I, is isolated by conventional procedures such as washing, stripping, crystallization, filtration, chromatography, and the like.

Utility

The compounds of the present invention are useful in controlling a wide variety of pests.

These compounds are active as fungicides and are particularly effective in controlling a variety of fungi which are deleterious to plants, including plant fungal infections. These compounds are particularly effective in controlling certain leaf blights caused by organisms such as *Phytophthora infestans*. In addition, some of these compounds are useful in controlling blights caused by organisms such as *Alternaria solani* and *Septoria apii*, rice blast caused by the organism *Piricularia oryzae* and powdery mildews such as that caused by *Erisiphe polygoni*. However, some of the compounds of this invention may be more fungicidally active than others against particular fungi.

In addition, some of the compounds of this invention show antibacterial activity and may inhibit bacterial growth.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus, and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersants. These compositions normally contain from about 5% to 80% fungicide, and the rest inert material, which include dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant-growth regulators, fertilizers, etc.

A further understanding of the invention can be had in the following non-limiting Examples. Wherein, unless expressly stated to the contrary, all temperature ranges refer to the Centigrade system and the term "ambient" or "room temperature" refers to about 20° C. to about 25° C. The term "percent" refers to gram moles. The term "equivalent" refers to a quantity of reagent equal in moles, to the moles of the preceding or succeeding reagent recited in that example in terms of finite moles or finite weight or volume. Also, unless expressly stated to the contrary, geometric isomer and racemic mixtures are used as starting materials and correspondingly, isomer mixtures are obtained as products.

EXAMPLES

Example 1

Preparation of N-Cyanomethyl-4-nitrobenzamide

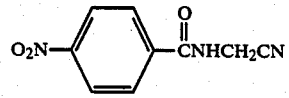

To a stirred mixture of 9.3 g (0.1 mole) aminoacetonitrile hydrochloride in 200 ml chloroform, 20.2 g (0.2 moles) triethylamine were added at once. After stirring one hour, 18.6 g (0.1 mole) p-nitrobenzoyl chloride were added in portions over about 15 minutes. The reaction mixture was stirred about 1½ hours. Ice water, 100 ml, was added, resulting in separation of solids. The reaction mixture was allowed to stand in an ice bath for 30 minutes and then was filtered. The solids were air dried, washed with 200 ml water and then filtered to give yellow solids. The solids were dried in a vacuum oven at 50° C. until constant weight was attained, yielding 18.0 g of the above-identified product as a light yellow solid, melting point 147° C. to 149° C.

Example 2

Preparation of
N-Cyanomethyl-N-(1,1,2,2-tetrachloroethylthio)-4-nitrobenzamide

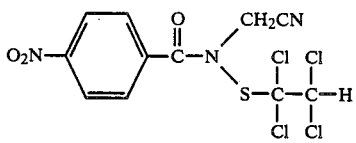

To a stirred mixture of 5.0 g (0.025 mole) N-cyanomethyl-4-nitrobenzamide (the product of Example 1) and 5.7 g (0.024 mole) 1,1,2,2-tetrachloroethylsulfenyl chloride in 125 ml methylene chloride, 3.0 g (0.030 mole) triethylamine in 25 ml methylene chloride were dropped in over 42 minutes. The reaction mixture was stirred 1½ hours. The solvent was washed three times with 75 ml portions of water, dried over magnesium sulfate and stripped to give 9.3 g beige solids. The solids were taken up in 25 ml toluene, treated with charcoal and filtered. The filtrate was cooled in an ice bath; solids separated. The solids were filtered, washed with hexane and air dried to give 6.0 g of the above-identified product as a yellow solid, melting point 123° C. to 128° C.

A 1.0 g portion was recrystallized from 25 ml toluene. The resulting solids were washed with hexane and air dried to give 0.6 g yellow solids, melting point 128° C. to 131° C.

Elemental analysis for $C_{11}H_7Cl_4N_3O_3S$ showed: calculated %C 32.78, %H 1.74, and %N 10.43; found %C 36.54 %H 2.4 and %N 11.94.

Example 3

Preparation of 2-Amino-2-methylpropionitrile

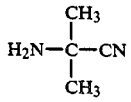

To a mixture of 55.45 g (0.88 moles) ammonium formate in 100 ml water, 51.2 g (0.88 moles) acetone were added. The reaction mixture was cooled in an ice bath, while 57 g (0.88 moles) potassium cyanide were spooned in over an hour. The ice bath was removed and the reaction mixture was stirred an additional 3½ hours. The reaction mixture was shaken with 150 ml methylene chloride in a separating funnel; the phases were separated. The organic layer was dried over magnesium sulfate and distilled over in the Rotavapor ® to give 52.3 g of the above-identified product as a colorless liquid.

Example 4

Preparation of
2-(o-Chlorobenzamido)-2-methylpropionitrile

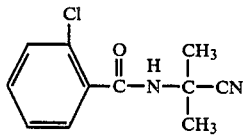

To a stirred mixture of 8.4 g (0.1 mole) 2-amino-2-methylpropi,onitrile (the product of Example 3) and 12.0 g (0.12 moles) triethylamine in 125 ml methylene chloride, 17.5 g (0.1 mole) o-chlorobenzoyl chloride in 25 ml methylene chloride were dropped in over one hour in a moderately exothermic addition reaction. The reaction mixture was stirred 15 minutes. The reaction mixture was washed twice with water (200 ml, then 100 ml), dried over magnesium sulfate and stripped to give 23.3 g of brown oil. Hexane, 25 ml was rubbed into the oil, which crystallized when the mixture was cooled in an ice bath. The solids were filtered and air dried to give 19.6 g of the above-identified product as a yellow solid, melting point 59° C. to 65° C.

Example 5

Preparation of
N-(1,1,2,2-tetrachloroethylthio)-2-(o-chlorobenzamido)-2-methylpropionitrile

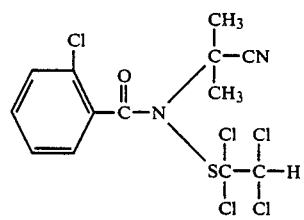

To a stirred mixture of 6.3 g (0.028 mole) 2-(o-chlorobenzamido)-2-methylpropionitrile (the product of Example 4) and 7.3 g (0.031 mole) 1,1,2,2-tetrachloroethylsulfenyl chloride in 125 ml methylene chloride, 3.6 g (0.036 mole) triethylamine in 25 ml methylene chloride were dropped in over about 30 minutes. The reaction mixture was stirred an additional 15 minutes. The reaction mixture was washed with 75 ml water three times, dried over magnesium sulfate, and then stripped to give 11.5 g of brown oil. Hexane was added, but as crystallization of the oil occurred, the hexane was decanted. The oil was taken up in 50 ml chloroform and the resulting solution chromatographed on about 125 g silica gel, eluting with chloroform. Cuts 3 to 9 of the chloroform eluate were combined and then stripped to give 3.5 g of the above-identified product, as a brown oil which slowly crystallized upon standing at room temperature.

Elemental analysis for $C_{13}H_{11}Cl_5N_2OS$ showed: calculated %C 37.13, %H 2.62, and %N 6.66; found %C 37.29, %H 2.71, and %N 6.61.

Example 6

Preparation of N-Cyanomethyl phenylacetamide

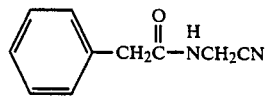

(a) A mixture of 27.2 g (0.2 moles) phenylacetic acid and 28 g (0.22 moles) oxalyl chloride in 150 ml methylene chloride were stirred for 24 hours. Excess reagent and solvent were removed by stripping to give 30.8 g of phenylacetyl chloride, which was used in step (b) without further isolation.

a stirred mixture of 18.5 g (0.2 moles)

(b) To aminoacetonitrile hydrochloride and 40 g (0.4 moles) triethylamine in 300 ml chloroform which was then cooled in an ice bath, the acid chloride from step (a) in 50 ml chloroform was dropped in over 60 minutes. The reaction mixture was washed three times with 200 ml water, dried over magnesium sulfate and stripped to give an oil. The oil was rubbed with 50 ml hexane and immediately solidified to give 30.4 g of beige solids, melting point 87° C. to 91° C.

A 1.0 g portion was recrystallized from toluenehexane to give 0.8 g of a white solid, melting point 91° C. to 92° C.

Elemental analysis for $C_{10}H_{10}N_2O$ showed: calculated %C 68.94, %H 6.80, and %N 16.07; found %C 69.8, %H 5.92, and %N 16.59.

Example 7

Preparation of N-Cyanomethyl-N-(trichloromethylthio) phenylacetamide

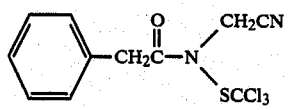

To a stirred mixture of 4.9 g (0.028 mole) N-cyanomethyl phenylacetamide (the product of Example 6) and 5.7 g (0.031 mole) trichloromethylsulfenyl chloride in ml methylene chloride which had been cooled in an ice bath, 3.5 g (0.035 mole) triethylamine in 25 ml methylene chloride were dropped in over 20 minutes. The reaction mixture was washed three times with 75 ml portions of water, dried over magnesium sulfate and stripped to give 8.0 g of a dark brown oil, which failed to crystallize.

The oil was applied to a column of 125 g silica gel and eluted with chloroform to give 3.6 g of a dark brown oil which crystallized upon cooling to room temperature.

A little of the solid was crystallized from hexane with charcoal treatment to give a grayish solid, melting point 79-81° C.

Elemental analysis for $C_{11}H_9Cl_3N_2OS$ showed: calculated %C 40.81, %H 2.80, and %N 8.65; found %C 40.68, %H 3.06, and %N 8.53.

Example 8

Preparation of N-Cyanomethyl-2-chlorobenzamide

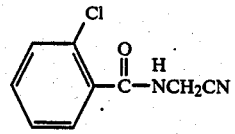

To a stirred mixture of 9.3 g (0.1 mole) aminoacetonitrile hydrochloride and 20.2 g (0.2 moles) triethylamine in 200 ml chloroform, 17.5 g (0.1 mole) o-chlorobenzoyl chloride in 25 ml methylene chloride were dropped in over 30 minutes in a moderately exothermic addition. The reaction mixture was washed twice with 75 ml water. On the second washing, solids separated which were filtered and washed well with water. Beige solids were obtained.

Additional solids were obtained by evaporating the methylene chloride. The combined solids were vacuum oven dried to give 16.0 g of the above-identified product as a beige solid, melting point 117° C. to 120° C.

Example 9

Preparation of N-Cyanomethyl-N-trichloromethylthio-2-chlorobenzamide

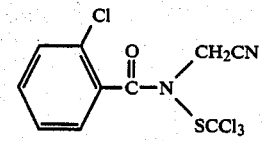

To a stirred mixture of 5.0 g (0.026 mole) N-Cyanomethyl-2-chlorobenzamide (the product of Example 8) and 5.3 g (0.029 mole) trichloromethylsulfenyl chloride in 125 ml methylene chloride, 3.2 g (0.032 mole) triethylamine in 25 ml methylene chloride were dropped in over 35 minutes. The reaction mixture was stirred about 25 minutes. The reaction mixture was washed three times with 75 ml water, dried over magnesium sulfate and stripped to give a brown oil. Hexane (25 ml) was added to the oil which crystallized when cooled in an ice bath.

The solids were recrystallized from 25 ml toluene, treating with carbon, and washed with hexane to give 2.7 g of white solids, melting point 62° C. to 67° C.

An additional 2.3 g of white solids, melting point 62° C. to 65° C. were obtained from the mother liquor.

Elemental analysis for $C_{10}H_6Cl_4N_2OS$ showed: calculated %C 34.91, %H 1.74, and %N 8.14; found %C 34.97, %H 1.9, and %N 8.27.

Example 10

Preparation of N-Cyanomethyl-o-toluamide

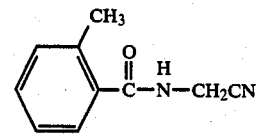

To a solution of 9.3 g (0.1 mole) aminoacetonitrile hydrochloride and 20.2 g (0.2 moles) triethylamine in 200 ml chloroform which had been stirred about two hours to give a clear solution, 15.5 g (0.1 mole) o-tolylbenzoyl chloride in 25 ml methylene chloride were dropped in over 30 minutes in a moderately exothermic addition reaction. The reaction mixture was washed three times with 75 ml water, dried over magnesium sulfate and stripped to give beige solids. The solids were washed with hexane and air dried to give 15.9 g of the above-identified product as a beige solid, melting point 102° C. to 105° C.

Example 11

Preparation of N-Cyanomethyl-N-trichloromethylthio-o-toluamide

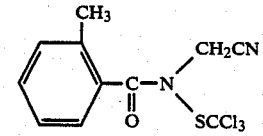

To a stirred mixture of 5.0 g (0.029 mole) N-cyanomethyl-o-toluamide (the product of Example 10) and 5.8 g (0.031 mole) trichloromethylsulfenyl chloride in 125 ml methylene chloride, 3.6 g (0.036 mole) triethylamine in 25 ml methylene chloride were added dropwise over 40 minutes. The reaction mixture was stirred 30 minutes. The reaction mixture was washed three times with 75 ml water, dried over magnesium sulfate and stripped to give a brown oil. The oil did not crystallize when rubbed with hexane. The oil was column chromatographed through 125 g of silica gel, eluting with chloroform to give 5.6 g of a glass-like product which crystallized partly upon cooling to room temperature.

The semi-crystalline product was recrystallized from 25 ml toluene, treating with activated carbon, 3.6 g of the above-identified product were obtained after a hexane wash, as a white solid, melting point 84° C. to 87° C.

Elemental analysis for $C_{11}H_9Cl_3N_2OS$ showed: calculated %C 40.83, %H 2.78, and %N 8.66; found %C 41.17, %H 2.84, and %N 8.84.

Example 12

Preparation of N-Cyanomethyl-1-naphthamide

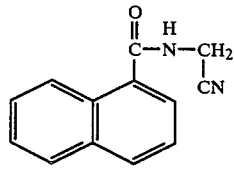

(a) a mixture of 17.2 g (0.1 mole) 1-naphthoic acid, 14 g (0.11 moles) oxalyl chloride, 150 ml methylene chloride and three drops DMF (dimethylformamide) were stirred for about 24 hours. The clear reaction mixture was stripped to give about 19.1 g of the 1-naphthoyl chloride as a brown liquid which was used in step (b) without further isolation.

(b) To a solution of 9.3 g (0.1 mole) aminoacetonitrile hydrochloride and 20.2 g (0.2 moles) triethylamine in 200 ml chloroform which had been stirred for about 15 minutes to give a clear solution, the naphthoyl chloride from step (a) in 25 ml methylene chloride was dropped in over about 30 minutes in a slightly exothermic addition. The reaction mixture was stirred 20 minutes, and then was mixed with 200 ml ice water. A precipitate formed immediately; however, the mixture was cooled in an ice bath for about 15 minutes before being filtered. The precipitate was filtered, washed with 100 ml water and vacuum dried at about 55° C. to a constant weight, to give 18.7 g of the above-identified product as a beige solid, melting point 160° C. to 163° C.

Example 13

Preparation of N-Cyanomethyl-N-(1,1,2,2-tetrachloroethylthio)-1-naphthamide

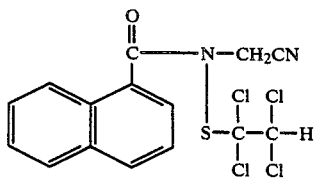

To a stirred mixture of 5.0 g (0.024 N-cyanomethyl-1-naphthamide (the product of Example 11) and 6.2 g (0.026 mole) 1,1,2,2-tetrachloroethylsulfenyl chloride in 125 ml methylene chloride, 3.0 g (0.030 mole) triethylamine in 25 ml methylene chloride were dropped in over 40 minutes. The reaction mixture was stirred 30 minutes. The reaction mixture was washed three times with 75 ml portions of water, dried over magnesium sulfate, and stripped down to a volume of 50 ml. The methylene chloride solution was then chromatographed on a column containing about 125 g silica gel, eluting with methylene chloride. The eluate was stripped to give 4.3 g of the above-identified product as an amber glass which tended to crystallize slowly.

Elemental analysis for $C_{15}H_{10}Cl_4N_2OS$ showed: calculated %C 44.15, %H 2.45, and %N 6.87; found %C 44.07, %H 2.67, and %N 6.98.

Example 14

Preparation of N-Cyanomethyl-N-trichloromethylthio-1-naphthamide

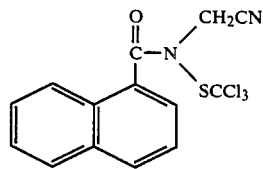

To a stirred mixture of 5.0 g (0.024 mole) N-cyanomethyl-1-naphthamide (the product of Example 11) and 4.9 g (0.26 mole) trichloromethylsulfenyl chloride in 125 ml methylene chloride, 2.9 g (0.29 mole) triethylamine in 25 ml methylene chloride were dropped in over 40 minutes. The reaction mixture was washed three times with 75 ml water, dried over magnesium sulfate and stripped to give 8.8 g of a dark oil.

The oil was taken up in chloroform and chromatographed on 125 g of silica gel, eluting with chloroform to give 4.8 g of the above-identified product as a light brown glass.

Elemental analysis for $C_{14}H_9Cl_3N_2OS$ showed: calculated %C 46.76, %H 2.50, and %N 7.80; found %C 45.08, %H 2.48, and %N 7.67.

Example 15

Preparation of 2-(o-Carbmethoxybenzamido)-2-methylpropionitrile

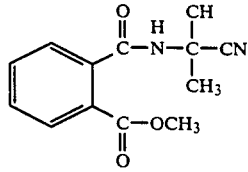

(a) A mixture of 18.0 g (0.1 mole) phthalic acid monomethyl ester, 14 g (0.11 moles) oxalylchloride, 150 ml methylene chloride and three drops DMF (dimethylformamide) were stirred for about 18 hours with evolution of gas. The mixture was stripped to give the acid chloride which was used in step (b) without further isolation.

(b) To a stirred mixture of 8.4 g (0.1 mole) 2-amino-2-methyl-propionitrile (the product of Example 3) and 12 g (0.12 moles) triethylamine in 125 ml methylene chloride cooled in an ice bath, the acid chloride from step (a) in 25 ml methylene chloride was dropped in over about 30 minutes. The reaction mixture was washed once with 75 ml ice water, once with 10 ml concentrated hydrochloric acid diluted to 75 ml with ice water and again with 75 ml ice water. The mixture was stripped to give 20 g of viscous oil that soon solidified. The solids were crystallized from toluene to give 11.8 g of the above-identified product, as a white solid, melting point 100° C. to 101° C.

Elemental analysis for $C_{13}H_{14}N_2O_3$ showed: calculated %C 63.42, %H 5.73, and %N 11.37; found %C 65.5, %H 6.03, and %N 12.11.

Example 16

Preparation of 2-(o-Carbmethoxybenzamido)-N-(1,1,2,2-tetrachloroethylthio)-2-methylpropionitrile

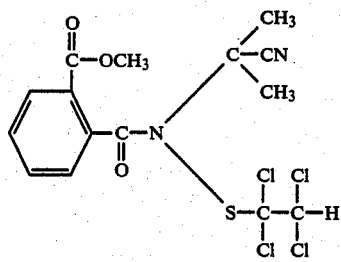

To a stirred mixture of 4.5 g (0.018 mole) 2-(o-Carbmethoxybenzamido)-2-methylpropionitrile (the product of Example 15) and 4.7 g (0.020 mole) 1,1,2,2-tetrachloroethylsulfenyl chloride in 125 ml methylene chloride, 2.4 g (0.024 mole) triethylamine in 25 ml methylene chloride were dropped in over 45 minutes. The reaction mixture was stirred for 15 minutes. The reaction mixture was washed three times with 75 ml water, dried over magnesium sulfate, and stripped to give 8.2 g of an amber oil. Chloroform, 50 ml, was added to the oil. The resulting mixture was chromatographed through about 125 g silica gel, eluting with chloroform to give 2.3 g of the above-identified product as an amber oil which crystallized upon cooling to room temperature.

Elemental analysis for $C_{15}H_{14}Cl_4N_2O_3S$ showed: calculated %C 40.57, %H 3.15, and %N 6.31; found %C 41.63, %H 3.28, and %N 6.82.

Example 17

Preparation of N-Cyanomethyl Acetamide

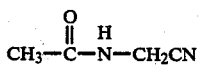

A mixture of 9.3 g (0.1 mole) aminoacetonitrile hydrochloride and 20.2 g (0.2 mole) triethyl amine in 200 ml chloroform were stirred together for one-half hour, giving a clear solution. To that mixture 7.9 g (0.1 mole) acetyl chloride in 25 ml methylene chloride were added over 30 minutes. The reaction mixture was stripped. The resulting solids were taken up with 100 ml glyme; the resulting mixture was shaken, allowed to stand overnight, and then filtered. The filtrate was stripped to give 10 g of a brown oil which immediately solidified. The solids were washed with hexane to give 9.9 g of the above-identified product, as beige solids, melting point 65°–69° C.

Example 18

Preparation of N-Cyanomethyl-N-(1,1,2,2-tetrachloroethylthio) acetamide

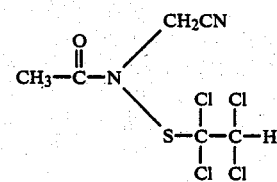

To a stirred mixture of 4.9 g (0.05 mole) N-cyanomethyl acetamide (the product of Example 17), and 11.7 g (0.05 mole) 1,1,2,2-tetrachloroethylsulfenyl chloride in 125 ml methylene chloride, 5.1 g (0.06 mole) [(0.05 mole)] triethylamine in 25 ml methylene chloride were added dropwise over 15 minutes. The reaction mixture was stirred for 30 minutes, washed three times with 50 ml ice water, dried over magnesium sulfate and stripped to give a red oil. The oil was chromatographed on a column of 165 g silica gel; eluting with chloroform to give 3.2 g of the above-identified product, as a red oil.

Elemental analysis for $C_6H_6Cl_4N_2OS$ showed: calculated %C 24.35, %H 2.04, and %N 9.47; found %C 24.32, %H 2.36, and %N 9.32.

Example 19

Preparation of N-Cyanomethyl-2-chloroacetamide

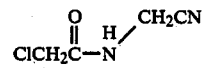

A mixture of 46.3 g (0.50 moles) aminoacetonitrile hydrochloride, 100 g (0.89 mole) chloroacetylchloride and 375 ml chloroform (which had been water washed to remove ethanol) was stirred at reflux for 7.0 hours. The solids gradually dissolved. The reaction mixture was filtered hot from a little tars. The product began to separate immediately, as the reaction mixture cooled. After cooling, the slurry was filtered before stripping at the water pump. The solid residue was removed by slurrying with hexane. Two crops were thus obtained: 62.4 g of an almost white solid, melting point 84°–87° C. and 63.3 g of a yellowish solid, melting point 82°–87° C.

Example 20

Preparation of N-Cyanomethyl-N-(1,1,2,2-tetrachloroethylthio)-2-chloroacetamide

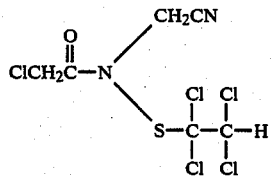

To a stirred mixture of 6 g (0.045 mole) N-cyanomethyl-2-chloroacetamide (the product of Example 19) and 10.6 g (0.045 mole) 1,1,2,2-tetrachloroethylsulfenyl chloride in 125 ml methylene chloride which was cooled in an ice bath, 4.6 g (0.045 mole) triethylamine in 25 methylene chloride were added dropwise over 15 minutes. After the addition was complete, the ice bath was removed; stirring of the mixture continued for 1½ hours. The reaction mixture was washed three times with 50 ml ice water, dried over magnesium sulfate and stripped to give 13.5 g of dark brown oil. The oil was washed with hexane and then taken up in 50 ml chloroform. The chloroform solution was chromatographed on a 165 g silica gel column, and eluted with chloroform, to give 6.3 g of the above-identified product, as an orange oil.

Elemental analysis for $C_6H_5C_5N_2OS$ showed: calculated %C 21.81, %H 1.53, and %N 8.48; found %C 21.90, %H 1.66, and %N 9.7.

Example 21

Preparation of N-Cyanomethyl trichloroacrylamide

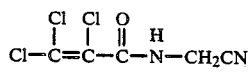

A stirred mixture of 38.8 g (0.2 moles) trichloroacryloyl chloride, 18.5 g. (0.2 moles) aminoacetonitrile hydrochloride and .150 ml chloroform was refluxed for thirty hours, with evolution of gas and dissolution of most of the aminoacetonitrile hydrochloride. The mixture was filtered hot to remove unreacted aminoacetonitrile hydrochloride. The filtrate was stripped to give an oil. The oil was rubbed with hexane and soon solidified to give 36.1 g of the above-identified product as an off-white solid, which liquified at about 56°–59° C. A small portion of product was recrystallized from a benzene-hexane mixture to give a white solid, melting point 58°–60° C.

Elemental analysis for $C_3$—$H_3Cl_3N_2O$ showed: calculated %Cl 49-84, found %Cl 50.0.

Example 22

Preparation of N-Cyanomethyl-N-(1,1,2,2-tetrachloroethylthio) trichloroacrylamide

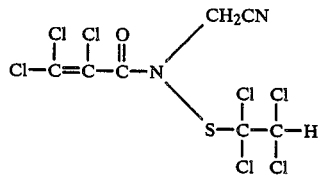

A mixture of 5.0 g. (0.023 moles) N-cyanomethyl trichloroacrylamide (the product of Example 21) and 5.5 g (0.023 moles) 1,1,2,2-tetrachloroethyl-sulfenyl chloride in 75 ml methylene chloride were stirred together to give a clear solution. The resulting mixture was cooled in an ice bath; then 2.2 g (0.028 moles) pyridine in 25 ml methylene chloride were added over twenty minutes. The ice bath was removed; stirring was continued for 23 hours. (TLC monitored the course of the reaction). The reaction mixture was cooled again in an ice bath. Triethylamine, 2.4 g (0.024 moles) in 25 ml methylene chloride was added over fifteen minutes; the mixture was stirred for one hour. The solvent was stripped to give an oil. The oil was chromatographed on a column of 165 g silica gel and eluted with benzene to give 5.4 g of the above-identified product which slowly solidified on standing to give a solid which liquified at 70°–75° C.

Elemental analysis for $C_7H_3Cl_7N_2Os$ showed: calculated %S 7.80 and %C 60.33; found %S 8.0 and %C 56.8.

Compounds prepared in accordance and with Examples 1 to 22 are found in Tables I and II.

Example A

Bacterial Inhibition

Compounds of this invention were evaluated for in vitro bactericidal effectiveness by means of a bacterial inhibition test. This test is designed to measure the antibacterial activity of compounds in terms of degree of inhibition bacterial multiplication. The representative bacteria used were *Erwinia amylovora*, *Pseudomonas syringae* and *Xanthomonas vesicatoria*. Each compound to be tested was dissolved in acetone to give a 500 ppm concentration. Agar plates were inoculated using a micro sprayer with an suspension of the particular bacteria shortly (3 to 5 seconds) before treatment. The inoculated agar plates were then treated with the compound to be tested by spraying with a micro sprayer. The treated plates were incubated at 23.5° C. and the data was taken 24 hours after treatment. Antibacterial activities are measured by a zone of inhibited bacterial growth from the center of the agar plates and the deposit concentration in mg/cm² at the edge of the zone of inhibition ($ED_{99}$) The effectiveness of the compounds for antibacterial activity are reported in Table III in terms of the percent of the $ED_{99}$ of each compound of the $ED_{99}$ of the standard PMA (phenyl mercuric acetate).

Example B

Mycelial Inhibition

Compounds were evaluated for in vitro fungicidal effectiveness by means of a mycelial inhibition test. This test is designed to measure the fungitoxic activity of fungicidal chemicals in terms of their degree of inhibition of mycelium growth. Fungi used were *Pythium ultimum, Rhizoctonia solani, Fusarium moniloforme, Botrytis cinerea, Aspergillus niger* and *Ustilago hordeii.* Each compound to be tested was dissolved in acetone to 500 ppm concentration. Paper strips were infused with the particular mycelium growth by covering the paper with a potato dextrose broth culture of mycelial suspension. The papers were then placed on potato dextrose agar plates and sprayed by means of a micro sprayer with the fungicidal solution. The treated paper strips were incubated at 25° C. and the data is taken after 24 hours. Fungicidal activities are measured by a zone of inhibited mycelial growth from the center of the paper strip in terms of mg/cm² needed for 99½ control of the fungus ($ED_{99}$) The effectiveness of the compounds for fungicidal activity are reported in Table IV in terms of the percent of the $ED_{99}$ of the test compound of the $ED_{99}$ of the standard Difolatan ®.

Example C

Tomato Late Blight

Compounds were tested for the preventative control of the Tomato Late Blight organism *Phytophthora infestans.* Five- to six-week-old tomato (cultivar Bonny Best) seedlings were used. The tomato plants were sprayed with a 200-ppm suspension of the test compound in acetone, water and a nonionic emulsifier. The sprayed plants were then inoculated one day later with the organism, placed in an environmental chamber and incubated at 66° F. to 68° F. and 100% relative humidity for at least 16 hours. Following the incubation, the plants were maintained in a greenhouse for approximately seven days. The percent disease control provided by a given test compound was based on the percent disease reduction relative to untreated check plants. The results are tabulated in Table V.

Example D

Rice Blast

Compounds of this invention were tested for control of the Rice Blast organism *Piricularia oryzae*, using 10- to 14-day-old rice plant seedlings (Calrose M-9 variety). Seedling plants were sprayed with a 625-ppm solution of the test compound in acetone, water and a nonionic emulsifier (ORTHO X-77 spreader). The sprayed plants were inoculated one day later with the organism in an environmental chamber. After inoculation, the plants were kept in an environmental chamber for about 48 hours under conditions of about 72° F. to 75° F. and about 100% relative humidity. Following the incubation period, the plants were placed in a greenhouse with a temperature of about 72° F. and maintained with bottom watering for about 12 to 16 days. The percent disease control provided by a given test compound is based on a comparison of the percentage disease relative to the percent disease development on the untreated check plants:

$$\% \text{ Control} = 100 - 100 \times \left( \frac{\% \text{ disease in treated plants}}{\% \text{ disease in check}} \right)$$

The results are tabulated in Table V.

Example E

Tomato Early Blight

Compounds were tested for the control of the Tomato Early Blight organism *Alternaria solani conidia*. Tomato (variety Bonny Best) seedlings of six to seven weeks old were used. The tomato plants were sprayed with a 200-ppm solution of the test compound in an acetone-and-water solution containing a small amount of a nonionic emulsifier. The sprayed plants were inoculated one day later with the organism, placed in the environmental chamber and incubated at 66° F. to 68° F. and 100% relative humidity for 24 hours. Following the incubation, the plants were maintained in a greenhouse for about 12 days. Percent disease control was based on the percent disease development on untreated check plants. The results are tabulated in Table V.

Example F

Celery Late Blight

The Celery Late Blight tests were conducted using celery (Utah) plants 11 weeks old. The Celery Late Blight organism was *Septoria apii*. The celery plants were sprayed with 200-ppm solutions of the candidate toxicant mixed with acetone, water and a nonionic emulsifier. The plants were then inoculated with the organism and placed in an environmental chamber and incubated at 66° F. to 68° F. in 100% relative humidity for an extended period of time (approximately 48 hours). Following the incubation, the plants were allowed to dry and then were maintained in a greenhouse for approximately 14 days. The percent disease control provided by a given test compound is based on the percent disease reduction relative to untreated check plants. The results are reported in Table V.

Example G

Bean Powdery Mildew

Compounds were tested for the control of the Bean Powdery Mildew organism *Erysiphe polygoni*. Seedling bean plants were sprayed with a 250-ppm solution of the test compound in acetone, water and a nonionic emulsifier. The sprayed plants were then inoculated one day later with the organism. The plants were maintained for 10 days at temperatures of 68° F. at night with daytime temperatures of 72° F. to 80° F.; relative humidity was maintained at 40% to 60%. The percent disease control provided by a given test compound was based on the percent disease reduction relative to the untreated check plants. The results as percent control are tabulated in Table V.

Example H

Bean Rust

Compounds were evaluated for their ability to eradicate Bean Rust caused by *Uromyces phaseoli tipica* on pinto beans.

Pinto bean plants, variety Idaho 1-11, 16 (summer) or 19 (winter) days old were inoculated with a 50-ppm suspension of uredospores in water containing a small amount of nonionic surfactant. The inoculated plants were placed in an environmental chamber immediately after inoculation and incubated 20 hours. Following the incubation period, the plants were removed from the chamber and placed in a greenhouse maintained at 66° F. to 68° F. and 60% to 80% relative humidity. Two days after inoculation, the plants were treated by spraying with a 200-ppm solution of test compound in an acetone and water carrier formulation containing a small amount of nonionic surfactant. One or two replicate pots (each containing two plants) were used for each compound. In addition one or two replicate pots were sprayed with the same carrier formulation (without a test compound) as a control (hereinafter "untreated Checks"). The plants were kept in the greenhouse until evaluated. The plants were evaluated for disease control when disease symptoms were well developed on the untreated Checks, normally about 14 days after treatment. The percentage disease control (or eradication) provided by a test compound was based on the percent disease reduction relative to the untreated Checks. The results are reported in Table V.

TABLE I

Compounds of the Formula:

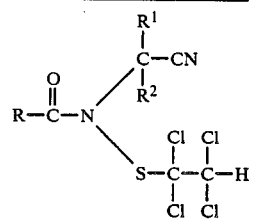

| Compound | R | R¹ | R² | Physical State | %C Calc. | %C Found | %H Calc. | %H Found | %N Calc. | %N Found | %S Calc. | %S Found | %Cl Calc. | %Cl Found |
|---|---|---|---|---|---|---|---|---|---|---|---|---|---|---|
| 1 43956 | phenyl | —H | —H | lt brown viscous oil | 36.9 | 37.43 | 2.23 | 2.31 | 7.83 | 7.9 | | | | |
| 2 44314 | phenyl | —CH₃ | —H | brown solid | 38.74 | 37.75 | 2.69 | 2.89 | 7.53 | 7.70 | | | | |
| 3 44109 | 2,3-dimethoxyphenyl | —H | —H | brown glass | 37.35 | 36.71 | 2.9 | 3.04 | 6.7 | 6.63 | | | | |
| 4 23976 | 2-fluorophenyl | —H | —H | yellow oil | | | | | | | 8.5 | 8.8 | 37.7 | 35.4 |
| 5 24128 | 4-chlorophenyl | —H | —H | dark-yellow oil | 33.65 | 33.46 | 1.81 | 1.83 | 7.13 | 7.14 | 8.17 | 8.8 | 45.18 | 41.5 |
| 6 44353 | 2-chlorophenyl | —CH₃ | —CH₃ | amber solid | 37.13 | 37.29 | 2.62 | 2.71 | 6.66 | 6.61 | | | | |
| 7 44037 | 2,3-dichlorophenyl | —H | —H | brown glass | 30.94 | 30.77 | 1.40 | 1.49 | 6.56 | 6.51 | | | | |
| 8 44039 | 2-nitrophenyl | —H | —H | beige solid, mp 124–127° C. | 32.78 | 33.85 | 1.74 | 1.75 | 10.43 | 11.0 | | | | |
| 9 44381 | 2-nitrophenyl | —CH₃ | —CH₃ | yellow solid | 36.22 | 35.92 | 2.55 | 2.6 | 9.75 | 9.8 | | | | |
| 10 43873 | 4-nitrophenyl | —H | —H | yellow solid, mp 128–131° C. | 32.78 | 36.54 | 1.74 | 2.4 | 10.43 | 11.94 | | | | |
| 11 44351 | 4-nitrophenyl | —CH₃ | —H | white solid, mp 174–180° C. | 34.56 | 35.45 | 2.16 | 2.02 | 10.08 | 10.62 | | | | |
| 12 44448 | 3-cyanophenyl | —H | —H | brown glass | 37.62 | 36.6 | 1.83 | 1.99 | 10.97 | 10.31 | | | | |
| 13 44266 | 2-(methoxycarbonyl)phenyl | —CH₃ | —CH₃ | amber solid | 40.57 | 44.63 | 3.15 | 3.28 | 6.31 | 6.82 | | | | |

TABLE I-continued

Compounds of the Formula:

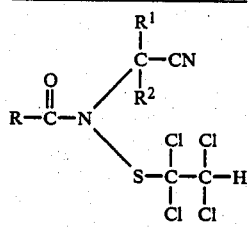

| Compound | R | $R^1$ | $R^2$ | Physical State | % C Calc. | % C Found | % H Calc. | % H Found | % N Calc. | % N Found | % S Calc. | % S Found | % Cl Calc. | % Cl Found |
|---|---|---|---|---|---|---|---|---|---|---|---|---|---|---|
| 14 46226 | H₃C—C=O / O / (2-methylphenyl) | —CH₃ | —CH₃ | solidified oil | 40.56 | 40.98 | 3.17 | 3.29 | 6.30 | 6.72 | | | | |
| 15 44450 | 1-naphthyl | —H | —H | brown glass | 44.15 | 44.07 | 2.45 | 2.67 | 6.87 | 6.98 | | | | |
| 16 44412 | C₆H₅—CH₂— | —H | —H | brown glass | 38.74 | 37.93 | 2.69 | 2.79 | 7.53 | 7.68 | | | | |
| 17 46071 | CH₃— | —H | —H | red oil | 24.35 | 24.32 | 2.04 | 2.36 | 9.47 | 9.32 | | | | |
| 18 45937 | ClCH₂— | —H | —H | brown oil | 21.81 | 21.90 | 1.53 | 1.66 | 8.48 | 9.70 | | | | |
| 19 24651 | Cl₂C=CCl— | —H | —H | beige solid mp 70–75° C. | | | | | | | 7.80 | 8.0 | 60.33 | 56.8 |
| 20 46006 | CH₃OCH₂— | —H | —H | solidified orange oil | 25.79 | 25.91 | 2.47 | 2.43 | 8.59 | 8.98 | | | | |
| 21 46665 | CH₃OCH₂— | —CH₃ | —H | red oil | | | | | | | | | | |

TABLE II

Compounds of the Formula:

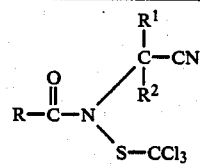

| Compound | R | $R^1$ | $R^2$ | Physical State | % C Calc. | % C Found | % H Calc. | % H Found | % N Calc. | % N Found | % S Calc. | % S Found | % Cl Calc. | % Cl Found |
|---|---|---|---|---|---|---|---|---|---|---|---|---|---|---|
| 22 43955 | phenyl | —H | —H | light yellow solid, mp 110–113° C. | 38.29 | 40.38 | 2.26 | 2.62 | 9.05 | 9.93 | | | | |
| 23 44313 | phenyl | —CH₃ | —H | amber solid | 40.83 | 41.21 | 2.78 | 2.99 | 8.66 | 9.87 | | | | |
| 24 44146 | phenyl | —CH₃ | —CH₃ | beige solid, mp 133–134° C. | 42.69 | 42.66 | 3.26 | 3.31 | 8.3 | 8.33 | | | | |
| 25 44112 | 2-methylphenyl | —H | —H | white solid, mp 84–87° C. | 40.83 | 41.17 | 2.78 | 2.84 | 8.66 | 8.84 | | | | |
| 26 44380 | 2-methylphenyl | —CH₃ | —CH₃ | white solid, mp 117–123° C. | 44.40 | 47.13 | 3.70 | 4.04 | 7.97 | 9.77 | 30.25 | 27.64 | 9.12 | 7.24 |

TABLE II-continued

Compounds of the Formula:

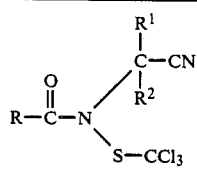

| Compound | R | R¹ | R² | Physical State | % C Calc. | % C Found | % H Calc. | % H Found | % N Calc. | % N Found | % S Calc. | % S Found | % Cl Calc. | % Cl Found |
|---|---|---|---|---|---|---|---|---|---|---|---|---|---|---|
| 27 44108 | 2,6-(OCH₃)₂-phenyl | —H | —H | off-white solid, mp 122–125° C. | 38.97 | 40.93 | 2.97 | 3.21 | 7.58 | 8.0 | | | | |
| 28 44215 | 2,6-(OCH₃)₂-phenyl | —CH₃ | —CH₃ | brown oil | 42.29 | 40.09 | 3.77 | 3.81 | 7.04 | 6.94 | | | | |
| 29 43824 | 2-F-phenyl | —H | —H | white solid, mp 92–96° C. | 36.65 | 37.35 | 1.85 | 2.00 | 8.54 | 9.32 | | | | |
| 30 44111 | 2-Cl-phenyl | —H | —H | white solid, mp 62–65° C. | 34.91 | 34.97 | 1.74 | 1.9 | 8.14 | 8.27 | | | | |
| 31 44352 | 2-Cl-phenyl | —CH₃ | —CH₃ | beige solid, mp 105–108° C. | 38.74 | 44.9 | 2.69 | 3.17 | 7.53 | 7.56 | | | | |
| 32 44036 | 2,3-Cl₂-phenyl | —H | —H | beige solid, mp 108–110° C. | 31.7 | 33.36 | 1.32 | 1.46 | 7.40 | 8.73 | | | | |
| 33 44038 | 2-NO₂-phenyl | —H | —H | yellow crystals, mp 72–74° C. | 33.87 | 34.66 | 1.69 | 1.99 | 11.85 | 12.52 | | | | |
| 34 44147 | 2-NO₂-phenyl | —CH₃ | —CH₃ | light yellow solid, mp 158–163° C. | 37.67 | 38.1 | 2.61 | 2.75 | 10.95 | 11.5 | | | | |
| 35 43872 | 4-NO₂-phenyl | —H | —H | yellow solid, mp 129–131° C. | 33.84 | 34.57 | 1.69 | 1.96 | 11.85 | 12.35 | | | | |
| 36 44350 | 4-NO₂-phenyl | —CH₃ | —H | beige solid, mp 152–153° C. | 35.84 | 38.77 | 2.17 | 2.31 | 11.40 | 12.02 | | | | |
| 37 44415 | 3-CN-phenyl | —H | —H | beige solid, mp 141–143° C. | 39.49 | 39.84 | 1.80 | 1.95 | 12.56 | 12.60 | | | | |
| 38 44449 | 3-CN-phenyl | —CH₃ | —CH₃ | beige solid, mp 129–131° C. | 43.06 | 43.36 | 2.76 | 3.01 | 11.59 | 11.74 | | | | |

TABLE II-continued

Compounds of the Formula:

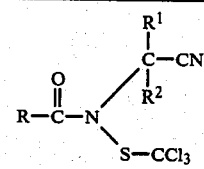

| Compound | R | R¹ | R² | Physical State | %C Calc. | %C Found | %H Calc. | %H Found | %N Calc. | %N Found | %S Calc. | %S Found | %Cl Calc. | %Cl Found |
|---|---|---|---|---|---|---|---|---|---|---|---|---|---|---|
| 39 44265 | (2-methylbenzoate, C(O)OCH₃ phenyl) | —CH₃ | —CH₃ | red solid | 42.5 | 42.18 | 3.29 | 3.4 | 7.08 | 7.07 | | | | |
| 40 44413 | (2-(N,N-dimethylcarbamoyl)phenyl) | —H | —H | off-white solid, mp 140–143° C. | 41.02 | 42.01 | 3.15 | 3.34 | 11.04 | 11.62 | | | | |
| 41 44447 | (2-phenylphenyl, biphenyl) | —H | —H | beige solid, mp 127–130° C. | 49.83 | 51.22 | 2.85 | 3.22 | 7.27 | 7.53 | | | | |
| 42 44218 | (1-naphthyl) | —H | —H | brown glass | 46.76 | 45.08 | 2.50 | 2.48 | 7.80 | 7.67 | | | | |
| 43 44414 | (1-naphthyl) | —CH₃ | —CH₃ | light yellow solid | 49.57 | 47.04 | 3.35 | 3.48 | 7.23 | 6.77 | | | | |
| 44 43825 | (benzyl, PhCH₂—) | —H | —H | brown solid, mp 79–81° C. | 40.81 | 40.68 | 2.80 | 3.06 | 8.65 | 8.53 | | | | |
| 45 46005 | ClCH₂— | —H | —H | white solid, mp 74–76° C. | 21.29 | 22.65 | 1.43 | 1.62 | 9.94 | 10.71 | | | | |
| 46 46073 | CH₃OCH₂— | —H | —H | white solid, mp 98–100° C. | 25.96 | 25.74 | 2.54 | 2.72 | 10.09 | 10.04 | | | | |

TABLE III

| Compound | Bacterial Inhibition Pseudo. | Erwin. | Xantho. |
|---|---|---|---|
| 1 43956 | 0 | 0 | 38 |
| 2 44314 | 0 | 39 | 100 |
| 3 44109 | 0 | 0 | 0 |
| 4 23976 | — | — | — |
| 5 24128 | 33 | 100 | 28 |
| 6 44353 | 0 | 0 | 16 |
| 7 44037 | 0 | 38 | 78 |
| 8 44039 | 0 | 24 | 51 |
| 9 44381 | 0 | 0 | 0 |
| 10 43873 | 25 | 19 | 56 |
| 11 44351 | 0 | 0 | 0 |
| 12 44448 | 0 | 0 | 40 |
| 13 44266 | 0 | 0 | 0 |
| 14 46226 | 0 | 0 | 0 |
| 15 44450 | 0 | 0 | 18 |
| 16 44412 | 0 | 0 | 0 |
| 17 46071 | 100 | 20 | 38 |
| 18 45937 | 100 | 40 | 100 |
| 19 24651 | — | — | — |
| 20 46006 | 100 | 20 | 94 |
| 21 46665 | 57 | 61 | 100 |
| 22 43955 | 0 | 0 | 0 |
| 23 44313 | 0 | 0 | 0 |
| 24 44146 | 0 | 0 | 0 |
| 25 44112 | 0 | 0 | 0 |
| 26 44380 | 0 | 0 | 100 |
| 27 44108 | 0 | 0 | 0 |
| 28 44215 | 0 | 0 | 0 |
| 29 43824 | 0 | 0 | 0 |
| 30 44111 | 0 | 0 | 0 |
| 31 44352 | 0 | 0 | 0 |
| 32 44036 | 0 | 0 | 14 |
| 33 44038 | 0 | 0 | 18 |
| 34 44147 | 0 | 0 | 0 |
| 35 43872 | 0 | 0 | 0 |
| 36 44350 | 0 | 0 | 0 |
| 37 44415 | 0 | 0 | 0 |
| 38 44449 | 0 | 0 | 0 |
| 39 44265 | 0 | 0 | 0 |
| 40 44413 | 0 | 0 | 0 |

TABLE III-continued

| | | Bacterial Inhibition | | |
|---|---|---|---|---|
| Compound | | Pseudo. | Erwin. | Xantho. |
| 41 | 44447 | 0 | 0 | 0 |
| 42 | 44218 | 0 | 0 | 0 |
| 43 | 44414 | 0 | 0 | 0 |
| 44 | 43825 | 0 | 0 | 0 |
| 45 | 46005 | 73 | 29 | 33 |
| 46 | 46073 | 16 | 12 | 18 |

Pseudo. = Pseudomonas syringae
Erwin. = Erwinia amylovora
Xantho. = Xanthomonas vesicatoria
— = not tested or test failed.

TABLE IV

| | | Mycelial Inhibition | | | | | |
|---|---|---|---|---|---|---|---|
| Compound | | Pyth. | Rhiz. | Fusar. | Botry. | Asper. | Ustil. |
| 1 | 43956 | 46 | 85 | 58 | 46 | 64 | 60 |
| 2 | 44314 | 27 | 160 | 0 | 140 | 65 | 72 |
| 3 | 44109 | 30 | 100 | 0 | 60 | 36 0 | 0 |
| 4 | 23976 | — | — | — | — | — | — |
| 5 | 24128 | 68 | 93 | 66 | 75 | 68 | — |
| 6 | 44353 | 0 | 88 | 48 | 38 | 0 | 63 |
| 7 | 44037 | 24 | 70 | 0 | 50 | 41 | 54 |
| 8 | 44039 | 48 | 90 | 0 | 79 | 0 | 50 |
| 9 | 44381 | 100 | 88 | 0 | 50 | 32 | 38 |
| 10 | 43873 | 100 | 100 | 80 | 88 | 44 | 38 |
| 11 | 44351 | 43 | 88 | 0 | 46 | 0 | 63 |
| 12 | 44448 | 38 | 44 | 0 | 95 | 0 | 55 |
| 13 | 44266 | 0 | 160 | 46 | 63 | 36 | 86 |
| 14 | 46226 | 12 | 44 | 37 | 100 | 81 | 36 |
| 15 | 44450 | 19 | 100 | 77 | 57 | 0 | 88 |
| 16 | 44412 | 45 | 113 | 61 | 55 | 63 | 48 |
| 17 | 46071 | 100 | 160 | 122 | 100 | 46 | 100 |
| 18 | 45937 | 100 | 100 | 72 | 100 | 45 | 100 |
| 19 | 24651 | 19 | 41 | 59 | 40 | 39 | — |
| 20 | 46506 | 100 | 61 | 58 | 55 | 170 | 53 |
| 21 | 46665 | 65 | 76 | 103 | 100 | 100 | 57 |
| 22 | 43955 | 0 | 23 | 0 | 0 | 0 | 23 |
| 23 | 44313 | 0 | 26 | 0 | 45 | 0 | 37 |
| 24 | 44146 | 0 | 0 | 0 | 0 | 0 | 0 |
| 25 | 44112 | 0 | 63 | 0 | 43 | 0 | 0 |
| 26 | 44380 | 0 | 0 | 0 | 0 | 0 | 0 |
| 27 | 44108 | 0 | 0 | 0 | 0 | 0 | 0 |
| 28 | 44215 | 0 | 0 | 0 | 0 | 0 | 0 |
| 29 | 43824 | 0 | 49 | 0 | 38 | 0 | 0 |
| 30 | 44111 | 0 | 58 | 0 | 26 | 19 | 27 |
| 31 | 44352 | 0 | 0 | 0 | 0 | 0 | 16 |
| 32 | 44036 | 0 | 24 | 0 | 43 | 44 | 33 |
| 33 | 44038 | 0 | 30 | 0 | 50 | 0 | 34 |
| 34 | 44147 | 25 | 50 | 0 | 50 | 0 | 0 |
| 35 | 43872 | 63 | 35 | 56 | 54 | 0 | 20 |
| 36 | 44350 | 0 | 0 | 0 | 0 | 0 | 19 |
| 37 | 44415 | 35 | 23 | 0 | 25 | 0 | 15 |
| 38 | 44449 | 0 | 25 | 0 | 0 | 0 | 0 |
| 39 | 44265 | 0 | 28 | 0 | 0 | 0 | 0 |
| 40 | 44413 | 0 | 0 | 0 | 0 | 0 | 0 |
| 41 | 44447 | 0 | 13 | 0 | 48 | 0 | 0 |
| 42 | 44218 | 0 | 32 | 0 | 0 | 0 | 0 |
| 43 | 44414 | 0 | 0 | 0 | 0 | 0 | 0 |
| 44 | 43825 | 0 | 49 | 0 | 35 | 0 | 21 |
| 45 | 46005 | 100 | 49 | 0 | 94 | 0 | 41 |
| 46 | 46073 | 75 | 20 | 0 | 28 | 0 | 31 |

Pyth. = Pythium ultimum
Rhiz. = Rhizoctonia solani
Fusar. = Fusarium moniloforme
Botry. = Botrytis cinerea
Asper. = Aspergillus niger
Ustil. = Ustilago hordeii
— = not tested or test failed.

TABLE V

| | | Fungicidal Activity | | | | | |
|---|---|---|---|---|---|---|---|
| Compound | | TLB | RB | TEB | CLB | BPM | BR |
| 1 | 43956 | 94 | 95 | 0 | 75 | 92 | 0 |
| 2 | 44314 | 100 | 96 | 0 | 95 | 50 | 0 |
| 3 | 44109 | 98 | 86 | 0 | 96 | 88 | 0 |
| 4 | 23976 | — | — | — | — | — | — |
| 5 | 24128 | 99 | — | 0 | — | 88 | 0 |
| 6 | 44353 | 100 | 94 | 44 | 100 | 90 | 0 |
| 7 | 44037 | 94 | 33 | 0 | 63 | 0 | 0 |
| 8 | 44039 | 91 | 40 | 0 | 69 | 0 | 0 |
| 9 | 44381 | 98 | 41 | 83 | 95 | 0 | 0 |
| 10 | 43873 | 99 | 78 | 79 | 71 | 0 | 0 |
| 11 | 44351 | 50 | 70 | 75 | 75 | 0 | 0 |
| 12 | 44448 | 93 | 75 | 90 | 50 | 0 | 0 |
| 13 | 44266 | 100 | 91 | 0 | 98 | 0 | 0 |
| 14 | 46226 | 63 | 67 | 30 | 57 | 0 | 0 |
| 15 | 44450 | 95 | 36 | 92 | 100 | 0 | 0 |
| 16 | 44412 | 94 | 75 | 67 | 83 | 71 | 0 |
| 17 | 46071 | 50 | 35 | 90 | 73 | 0 | 0 |
| 18 | 45937 | 39 | 98 | 78 | 100 | 13 | 0 |
| 19 | 24651 | 95 | — | 0 | 73 | 0 | 0 |
| 20 | 46006 | 47 | 25 | 33 | 70 | 14 | 6 |
| 21 | 46665 | 0 | 0 | 0 | — | 0 | 0 |
| 22 | 43955 | 81 | 33 | 14 | 0 | 66 | 0 |
| 23 | 44313 | 97 | 81 | 50 | 50 | 100 | 0 |
| 24 | 44146 | 91 | 93 | 79 | 56 | 100 | 0 |
| 25 | 44112 | 100 | 91 | 100 | 93 | 100 | 0 |
| 26 | 44380 | 64 | 0 | 17 | 0 | 0 | 0 |
| 27 | 44108 | 94 | 91 | 33 | 92 | 100 | 0 |
| 28 | 44215 | 50 | 0 | 37 | 50 | 90 | 0 |
| 29 | 43824 | 10 | 93 | 30 | 0 | 38 | 0 |
| 30 | 44111 | 94 | 71 | 93 | 92 | 100 | 0 |
| 31 | 44352 | 92 | 50 | 69 | 75 | 83 | 0 |
| 32 | 44036 | 94 | 0 | 92 | 72 | 100 | 0 |
| 33 | 44038 | 97 | 6 | 75 | 44 | 73 | 0 |
| 34 | 44147 | 94 | 93 | 86 | 69 | 100 | 0 |
| 35 | 43872 | 89 | 83 | 79 | 75 | 83 | 0 |
| 36 | 44350 | 69 | 30 | 6 | 78 | 13 | 0 |
| 37 | 44415 | 98 | 93 | 72 | 58 | 87 | 0 |
| 38 | 44449 | 91 | 46 | 60 | 94 | 88 | 0 |
| 39 | 44265 | 94 | 89 | 52 | 67 | 100 | 0 |
| 40 | 44413 | 69 | 75 | 50 | 0 | 99 | 0 |
| 41 | 44447 | 84 | 64 | 85 | 63 | 100 | 0 |
| 42 | 44218 | 95 | 78 | 75 | 81 | 100 | 0 |
| 43 | 44414 | 81 | 90 | 33 | 25 | 96 | 0 |
| 44 | 43825 | 50 | 95 | 43 | 93 | 100 | 0 |
| 45 | 46005 | 0 | 12 | 0 | 20 | 0 | 6 |
| 46 | 46073 | 0 | 10 | 67 | 0 | 0 | 0 |

TLB = Tomato Late Blight
RB = Rice Blast
TEB = Tomato Early Blight
CLB = Celery Late Blight
BPM = Bean Powdery Mildew
BR = Bean Rust
— = not tested or test failed.

What is claimed is:

1. A compound of the formula:

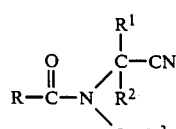

wherein R is alkyl of 1 to 10 carbon atoms, cycloalkyl of 3 to 10 carbon atoms, lower alkenyl of 2 to 6 carbon atoms or lower alkynyl of 2 to 6 carbon atoms, all optionally substituted with 1 to 4 halogen atoms; lower alkoxyalkylene; aryl of 6 to 12 carbon atoms, aralkyl of 7 to 16 carbon atoms, or substituted aryl or substituted aralkyl both substituted with 1 to 3 substituents independently selected from phenyl, lower alkyl of 1 to 6 carbon atoms, lower alkoxy of 1 to 6 carbon atoms, lower alkylthio of 1 to 6 carbon atoms, halogen, nitro, cyano,

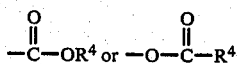

wherein R⁴ is hydrogen or lower alkyl of 1 to 6 carbon atoms,

wherein $R^5$ and $R^6$ are independently hydrogen or lower alkyl of 1 to 6 carbon atoms; $R^1$ and $R^2$ are independently hydrogen, or lower alkyl of 1 to 6 carbon atoms; and $R^3$ is lower alkyl of 1 to 3 carbon atoms substituted with 3 to 6 halogen atoms or trihalovinyl.

2. A compound according to claim 1 wherein R is naphthyl, phenyl or phenyl substituted with 1 to 2 substituents.

3. A compound according to claim 2 wherein said substituents are independently selected from halogen, nitro, cyano, methyl and methoxy.

4. A compound according to claim 3 wherein one substituent is in the ortho position.

5. A compound according to claim 4 wherein R is phenyl.

6. A compound according to claim 5 wherein $R^1$ is methyl, $R^2$ is hydrogen and $R^3$ is 1,1,2,2-tetrachloroethyl.

7. A compound according to claim 4 wherein R is o-tolyl.

8. A compound according to claim 7 wherein $R^1$ and $R^2$ are both hydrogen and $R^3$ is trichloromethyl.

9. A compound according to claim 2 wherein R is 1-naphthyl.

10. A compound according to claim 9 wherein $R^1$ and $R^2$ are both hydrogen.

11. A compound according to claim 10 wherein $R^3$ is 1,1,2,2-tetrachloroethyl.

12. A compound according to claim 1 wherein $R^3$ is 1,1,2,2-tetrachloroethyl.

13. A compound according to claim 1 wherein $R^3$ is trichloromethyl.

14. A compound according to claim 1 wherein $R^3$ is trichlorovinyl, 1,1,2,2-tetrachloroethyl, trichloromethyl, 2-fluoro-1,1,2,2-tetrachloroethyl, or fluorodichloromethyl.

15. A method of controlling fungi which comprises contacting said fungi or their growth environment with a fungicidally effective amount of a compound of claim 1.

16. A method of controlling fungi which comprises contacting said fungi or their growth environment with a fungicidally effective amount of a compound of claim 2.

17. A method of controlling fungi which comprises contacting said fungi or their growth environment with a fungicidally effective amount of a compound of claim 4.

18. A method of controlling fungi which comprises contacting said fungi or their growth environment with a fungicidally effective amount of a compound of claim 6.

19. A method of controlling fungi which comprises contacting said fungi or their growth environment with a fungicidally effective amount of a compound of claim 8.

20. A method of controlling fungi which comprises contacting said fungi or their growth environment with a fungicidally effective amount of a compound of claim 11.

21. A fungicidal composition which comprises an inert carrier and a fungicidally effective amount of a compound of claim 1.

22. A fungicidal composition which comprises an inert carrier and a fungicidally effective amount of a compound of claim 2.

23. A fungicidal composition which comprises an inert carrier and a fungicidally effective amount of a compound of claim 4.

24. A fungicidal composition which comprises an inert carrier and a fungicidally effective amount of a compound of claim 6.

25. A fungicidal composition which comprises an inert carrier and a fungicidally effective amount of a compound of claim 8.

26. A fungicidal composition which comprises an inert carrier and a fungicidally effective amount of a compound of claim 11.

* * * * *